(12) United States Patent
Takeuchi et al.

(10) Patent No.: US 8,961,401 B2
(45) Date of Patent: Feb. 24, 2015

(54) JOINT RING, BENDING TUBE OF ENDOSCOPE, ENDOSCOPE, AND MANUFACTURING METHOD FOR JOINT RING FOR ENDOSCOPE BENDING TUBE

(71) Applicant: Olympus Medical Systems Corp., Tokyo (JP)

(72) Inventors: Yasuo Takeuchi, Hachioji (JP); Keigo Takeshima, Hachioji (JP); Kiwamu Fujitani, Hachioji (JP); Motohiro Kuroda, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/952,199

(22) Filed: Jul. 26, 2013

(65) Prior Publication Data

US 2014/0018776 A1 Jan. 16, 2014

Related U.S. Application Data

(63) Continuation of application No. PCT/JP2013/052038, filed on Jan. 30, 2013.

(30) Foreign Application Priority Data

Feb. 20, 2012 (JP) ................. 2012-034215

(51) Int. Cl.
| | |
|---|---|
| *A61B 1/00* | (2006.01) |
| *A61B 1/008* | (2006.01) |
| *G02B 23/24* | (2006.01) |
| *A61B 1/005* | (2006.01) |
| *B29C 57/00* | (2006.01) |
| *F16B 7/00* | (2006.01) |

(52) U.S. Cl.
CPC ............ *A61B 1/008* (2013.01); *G02B 23/2476* (2013.01); *A61B 1/0008* (2013.01); *A61B 1/0011* (2013.01); *A61B 1/0055* (2013.01); *B29C 57/00* (2013.01); *F16B 7/00* (2013.01)
USPC ............................ 600/141; 600/139; 600/142

(58) Field of Classification Search
CPC ..... A61B 1/005; A61B 1/0055; A61B 1/0056
USPC ................................. 600/141–142
See application file for complete search history.

(56) References Cited

U.S. PATENT DOCUMENTS

| | | | | |
|---|---|---|---|---|
| 3,060,972 A | * | 10/1962 | Sheldon ................. | 138/120 |
| 4,108,211 A | * | 8/1978 | Tanaka .................. | 138/120 |
| 5,656,011 A | * | 8/1997 | Uihlein et al. .......... | 600/146 |
| 5,749,828 A | * | 5/1998 | Solomon et al. ........ | 600/141 |
| 6,408,889 B1 | * | 6/2002 | Komachi ................ | 138/120 |
| 6,641,528 B2 | * | 11/2003 | Torii ..................... | 600/142 |

FOREIGN PATENT DOCUMENTS

| | | |
|---|---|---|
| JP | 11-056760 A | 3/1999 |
| JP | 2001-061767 A | 3/2001 |
| JP | 2005-123085 A | 5/2005 |
| JP | 2008-188095 A | 8/2008 |
| JP | 2011-067423 A | 4/2011 |

* cited by examiner

*Primary Examiner* — Matthew J Kasztejna
(74) *Attorney, Agent, or Firm* — Scully, Scott, Murphy & Presser, PC

(57) ABSTRACT

A joint-ring for an endoscope-bending-tube that fits with and is fixed to a rigid-member on a distal end side, the joint-ring being formed by plastically deforming a tube-material, the joint-ring including a joint-ring-convex portion provided in the tube-material before the plastic deformation, configured to fit with distal end rigid concave portions of the distal end rigid-member to perform positioning, and protrudingly provided to the distal end side, a plastically deformed shape portion provided in the joint-ring such that an axial direction position thereof overlaps the joint-ring-convex-portion and formed by force of stretching along a circumferential surface in the plastic deformation, and joint-ring-convex-portions provided in the tube-material before the plastic deformation near both sides in the circumferential direction of the joint-ring-convex-portion to interrupt the force of stretching along the circumferential surface to keep the force from reaching the joint-ring-convex-portion to thereby prevent deformation of the joint-ring-convex-portion due to the plastic deformation.

11 Claims, 16 Drawing Sheets

JOINT RING, BENDING TUBE OF ENDOSCOPE, ENDOSCOPE, AND MANUFACTURING METHOD FOR JOINT RING FOR ENDOSCOPE BENDING TUBE

CROSS REFERENCE TO RELATED APPLICATION

This application is a continuation application of PCT/JP2013/052038 filed on Jan. 30, 2013 and claims benefit of Japanese Application No. 2012-034215 filed in Japan on Feb. 20, 2012, the entire contents of which are incorporated herein by this reference.

BACKGROUND OF THE INVENTION

1. Field of the Invention

The present invention relates to a joint ring for an endoscope bending tube configured to fit with and to be fixed to a rigid member on a distal end side or a proximal end side in an axial direction, a bending tube of an endoscope including the joint ring, an endoscope, and a manufacturing method for the joint ring for the endoscope bending tube.

2. Description of the Related Art

On a distal end side of an insertion portion of an endoscope, a bending portion configured to be bendable and a distal end rigid portion, in which an illumination optical system, an objective optical system, and the like are disposed, are connected. The bending portion is configured by connecting a plurality of joint rings to be formed in a bendable structure. A first joint ring on a most distal end side is configured to fit with and to be fixed to a distal end rigid member in the distal end rigid portion on a distal end side in an axial direction. A last joint ring on a most proximal end side of the bending portion fits with and is fixed to a rigid member at a distal end of a flexible portion having flexibility on a proximal end side in the axial direction. Various techniques for performing positioning in fitting the first joint ring and the distal end rigid member (or fitting the last joint ring and the rigid member of the flexible portion) have been proposed.

For example, Japanese Patent Application Laid-Open Publication No. H11-56760, for example, FIG. 5, describes an endoscope in which a distal end fixed frame 32 incorporating an objective optical system and a first joint ring 40 disposed on a most distal end side among a plurality of joints configuring a bending tube connected to the distal end fixed frame 32 are butted against each other in an axial direction of an insertion portion, connected, and fixed, the endoscope including a plurality of cutouts 46 elongated in the axial direction formed in the distal end fixed frame 32, a convex portion 44 protrudingly provided on a distal end side of the first joint 40 and configured to engage with one of the cutouts 46 and perform positioning of the first joint 40 and the distal end fixed frame 32 in a circumferential direction, and a protrusion 45 protrudingly provided in a middle of a circumferential surface of the first joint 40 and configured to engage with a rear end face of the distal end fixed frame 32 and perform positioning of the first joint 40 and the distal end fixed frame 32 in the axial direction.

For example, Japanese Patent Application Laid-Open Publication No. 2008-188095 describes a technique for preventing deformation of a cylindrical portion, which is a joint ring main body, in applying pressing to a projecting portion for coupling joint rings each other. That is, the publication describes a joint ring for an endoscope including a cylindrical portion, an opposed pair of tabular first projecting portions provided to project in an axial direction of one end edge of the cylindrical portion, and an opposed pair of tabular second projecting portions provided at the other end edge of the cylindrical portion to project in the axial direction and located to shift in a radial direction of the cylindrical portion by one step with respect to the first projecting portion, the first projecting portion and the second projecting portion being superimposed each other and rotatably coupled by inserting a coupling pin through coupling holes respectively formed therein and a plurality of the coupled first and second projecting portions being connected in series to configure a bendable bending portion, wherein a slit is formed between the second projecting portion and the cylindrical portion. It is described that, since the second projecting portion and the cylindrical portion are separated in a part because the slit is formed between the second projecting portion and the cylindrical portion, it is possible to prevent flat deformation of the cylindrical portion and perform pressing of the second projecting portion and it is possible to press the second projecting portion with high flatness (see paragraph [0014] and FIG. 2).

Further, although a technical field is different from an endoscope, Japanese Patent Application Laid-Open Publication No. 2005-123085 describes a technique for, in a coupling portion of a joint portion 46 and an anode 86 of an X-ray tube device, by forming a taper surface 46P in the joint portion 46 and forming a torus-shape curved surface 86P in the anode 86, dispersing stress according to a shape characteristic of the curved surface 86P even when the anode 86 is heated and tensile stress to an outer side occurs in a coupling portion 86a (see paragraphs [0032] and [0033], FIG. 9, etc.).

Incidentally, when a joint ring of a bending tube of an endoscope is machined, plastic deformation such as bulge processing is sometimes used. Bulge processing means pressing for performing blow molding for, after setting a tube material in a mold, closing the mold and, for example, compressing both ends of a material in an axial direction while filling high-pressure liquid in the mold to thereby cause the material to flow while extending the material to have a shape formed in the mold. Bulge processing is also referred to as hydroforming.

A state in applying such bulge processing to a joint ring is explained with reference to FIGS. 23 and 24. FIG. 23 is a side view showing the joint ring before the bulge processing. FIG. 24 is a side view showing the joint ring after the bulge processing.

In forming, in the joint ring, a shape portion for fitting with a distal end rigid member and performing positioning, two ways are conceivable, i.e., forming the shape portion before performing the bulge processing and forming the shape portion after performing the bulge processing.

First, when the shape portion for positioning is formed after the bulge processing, to perform machining without causing deformation in the joint ring, it is necessary to hold a joint ring with a mold having a shape matching an external shape of the joint ring.

On the other hand, before the bulge processing is performed, since a tube material generally has a cylindrical shape, even when it is necessary to use a mold, a general-purpose inexpensive mold can be used. Alternatively, even if slight deformation occurs in the tube material before the bulge processing, the tube material can be formed in a predetermined shape if the bulge processing is performed thereafter. Therefore, it is also possible to adopt an option for machining the tube material without holding the tube material with the mold.

Because of such a reason, it is desirable that the shape portion for fitting with the distal end rigid member and performing positioning is formed in the joint ring before the bulge processing is performed.

Therefore, as shown in FIG. 23, a concave portion 108a for positioning is formed in a joint ring 108 before the bulge processing. The concave portion 108a is a concave portion for performing at least positioning in a circumferential direction using an end face 108b extending along an axial direction.

When the bulge processing is applied to the joint ring 108 shown in FIG. 23, tensile force for expansion in a radial direction around an axis acts on the joint ring 108. After the bulge processing, the end face 108b for performing positioning in the circumferential direction changes as shown in FIG. 24.

SUMMARY OF THE INVENTION

A joint ring according to a first aspect of the present invention is a joint ring for an endoscope bending tube configured to fit with and to be fixed to a rigid member on a distal end side or a proximal end side in an axial direction, the joint ring being formed by plastically deforming a tube material, the joint ring including: a joint ring convex portion provided in the tube material before the plastic deformation and protrudingly provided toward the distal end side or the proximal end side in the axial direction, the joint ring convex portion including side end faces that fit with a positioning shape portion provided in the rigid member to perform positioning in a circumferential direction; a plastically deformed shape portion provided in the joint ring such that an axial direction position thereof overlaps an axial direction position of the joint ring convex portion and formed by force of stretching along a circumferential surface of the tube material in the plastic deformation; and joint ring concave portions provided in the tube material before the plastic deformation near both sides in the circumferential direction of the joint ring convex portion between the plastically deformed shape portion and the joint ring convex portion to block all lines in the circumferential direction connecting the plastically deformed shape portion and the joint ring convex portion and configured to interrupt the force of stretching along the circumferential surface to keep the force from reaching the joint ring convex portion to thereby prevent deformation of the joint ring convex portion due to the plastic deformation.

A bending tube of an endoscope according to a second aspect of the present invention is configured by turnably coupling a plurality of joint rings. A joint ring provided in a position adjacent to the rigid member is the joint ring for positioning according to the first aspect.

Further, an endoscope according to a third aspect of the present invention includes: the bending tube according to the second aspect; and the rigid member including the positioning shape portion that fits with the side end faces included in the joint ring convex portion of the joint ring for positioning to perform positioning.

A manufacturing method for a joint ring for an endoscope bending tube according to a fourth aspect of the present invention is a method including: forming, in a tube material, a joint ring convex portion protrudingly provided toward a distal end side or a proximal end side in an axial direction, the joint ring convex portion including side end faces that fit with a positioning shape portion provided in a rigid member to perform positioning in a circumferential direction, and joint ring concave portions located near the joint ring convex portion; and plastically deforming the tube material in which the joint ring convex portion and the joint ring concave portions are formed and forming a plastically deformed shape portion with force of stretching along a circumferential surface of the tube material in the plastic deformation such that an axial direction position overlaps an axial direction position of the joint ring convex portion, the joint ring concave portions being provided near both sides in the circumferential direction of the joint ring convex portion between the plastically deformed shape portion of the tube material and the joint ring convex portion to block all lines in the circumferential direction connecting the plastically deformed shape portion and the joint ring convex portion and interrupting the force of stretching along the circumferential surface to keep the force from reaching the joint ring convex portion to thereby prevent deformation of the joint ring convex portion due to the plastic deformation.

DETAILED DESCRIPTION OF THE PREFERRED EMBODIMENTS

Embodiments of the present invention are explained below with reference to the drawings.

First Embodiment

Figure 1:
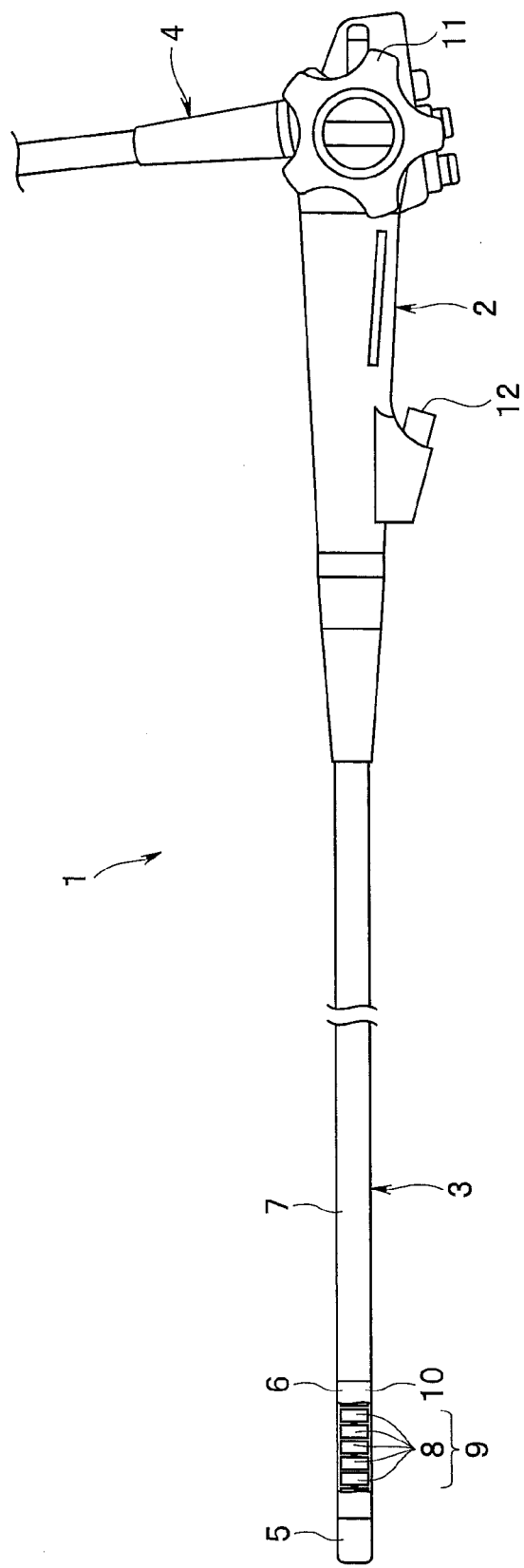
FIG. 1 is a side view showing a configuration of an endoscope in a first embodiment of the present invention.

FIGS. 1 to 21 are diagrams showing a first embodiment of the present invention. FIG. 1 is a side view showing a configuration of an endoscope.

An endoscope 1 may be any endoscope such as an electronic endoscope or an optical endoscope. However, in an example explained below, the endoscope 1 is the electronic endoscope.

As shown in FIG. 1, the endoscope 1 includes an operation portion 2, an elongated insertion portion 3 extended from the operation portion 2, and a universal cord 4 extended from a side surface of the operation portion 2.

The insertion portion 3 is a region inserted into a test object. In the case of a medical endoscope, the insertion portion 3 is inserted into, for example, a body cavity of a subject, which is the test object. In the case of an industrial endoscope, the insertion portion 3 is inserted into, for example, an engine, which is the test object. Note that, in an example explained below, the test object is the subject.

The insertion portion 3 includes a distal end rigid portion 5 provided at distal end, a bendable bending portion 6 connected to a proximal end of the distal end rigid portion 5, and a flexible portion 7 having flexibility connected to a proximal end of the bending portion 6.

In the distal end rigid portion 5, an objective lens for forming an optical image of the subject and an image pickup device configured to photoelectrically convert the optical image formed by the objective lens and output the optical image as an image signal are disposed. The image signal outputted from the image pickup device is transmitted to a not-shown CCU (camera control unit), to which the universal cord 4 is connected, via the insertion portion 3, the operation portion 2, and an image pickup cable 25 (see FIGS. 16 to 19) disposed in the universal cord 4. Further, the image signal is displayed as an endoscope image on a not-shown monitor or the like connected to the CCU.

For example, two illumination windows are provided in the distal end rigid portion 5. Illumination light from a not-shown light source device connected to the universal cord 4 is guided respectively to the two illumination windows via the universal cord 4, the operation portion 2, and, for example, two light guide fibers 26 (see FIGS. 16 to 19) disposed in the insertion portion 3. The illumination light is irradiated on the subject from the illumination windows.

Further, a channel opening functioning as both of a forceps channel and an air feeding and water feeding channel is provided in the distal end rigid portion 5. Fluid from a not-shown air feeding and water feeding device connected to the universal cord 4 is supplied via the universal cord 4, the operation portion 2, and a channel tube 24 (see FIGS. 16 to 19) disposed in the insertion portion 3. Alternatively, forceps are inserted from a forceps insertion port 12 provided in the operation portion 2 via a channel tube 24 in the insertion portion 3.

The bending portion 6 includes a bending tube 9 configured by coupling a plurality of joint rings 8 in series to be turnable and an angle rubber 10 having flexibility that covers an outer circumference of the bending tube 9. Among the plurality of joint rings 8 configuring the bending tube 9, the joint ring 8 on a most distal end side (referred to as first joint ring 8 or the like as appropriate) is fixed to the distal end rigid portion 5.

For example, distal ends of a pair of angle wires 23 (see FIGS. 16 to 19) are fixed to the distal end rigid portion 5. Proximal end sides of the angle wires 23 inserted through the insertion portion 3 are connected to a pulley that rotates in association with an angle knob 11 provided in the operation portion 2. When the angle knob 11 is operated, one of the pair of angle wires 23 is tensed and the other is loosened and the bending portion 6 is bent. Consequently, it is possible to change a direction of the distal end rigid portion 5.

Figure 2:
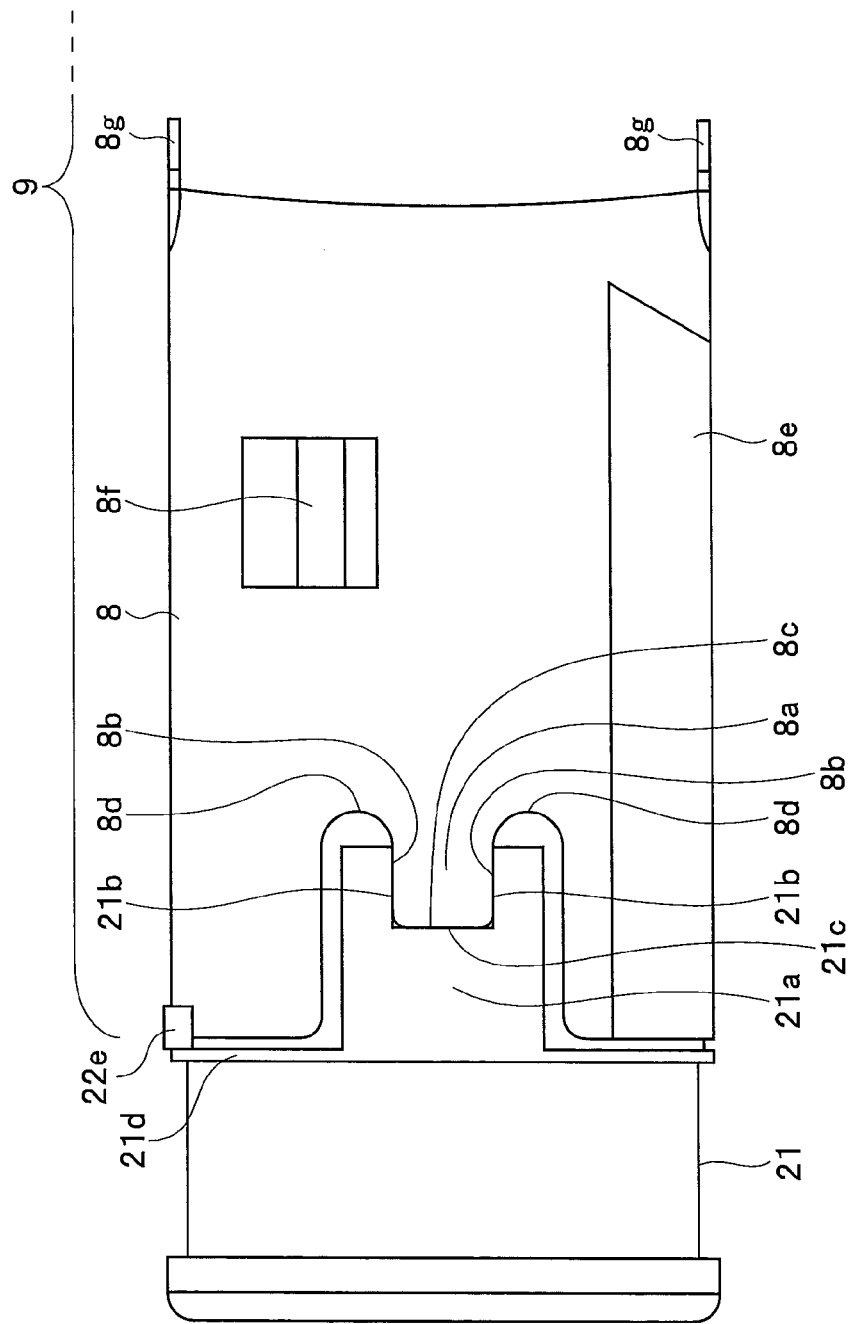
FIG. 2 is a side view showing a connection structure of a distal end rigid member and a first joint ring in the first embodiment.
Figure 3:
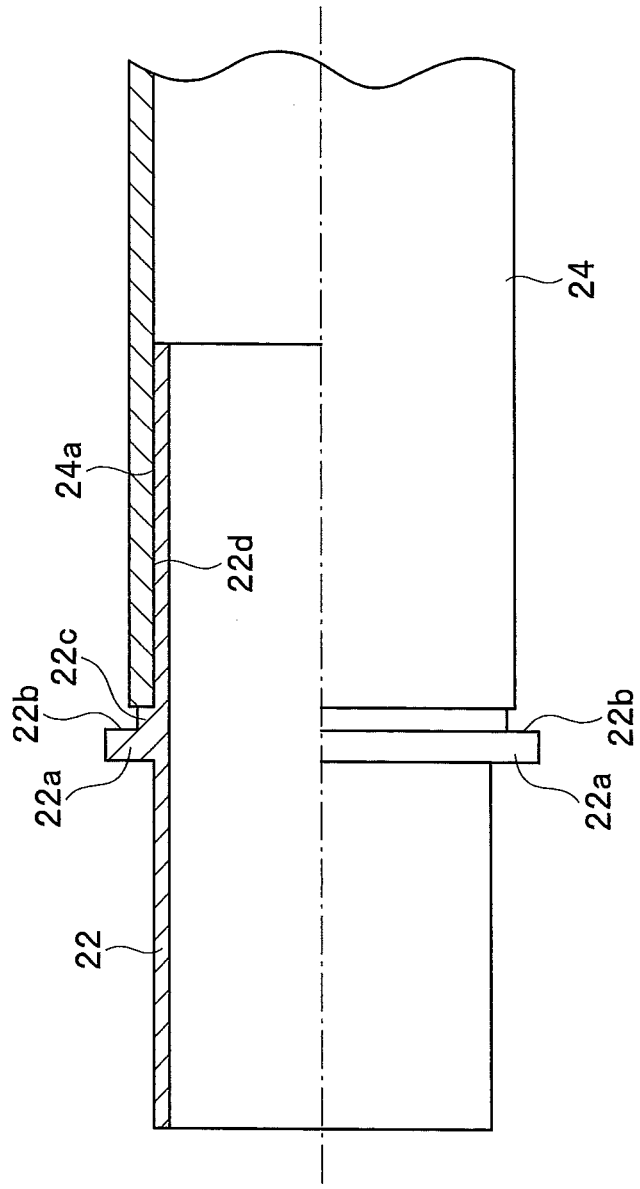
FIG. 3 is a sectional view taken along an axial direction showing a connection structure of a distal end portion of a forceps channel in the first embodiment.

FIG. 2 is a side view showing a connection structure of a distal end rigid member 21 and the first joint ring 8. FIG. 3 is a sectional view taken along an axial direction showing a connection structure of a distal end portion of the forceps channel.

The distal end rigid member 21 formed in a substantially cylindrical shape is provided in the distal end rigid portion 5. In the distal end rigid member 21, a distal end rigid concave portion 21a, which is a positioning shape portion that fits with the first joint ring 8 to position the first joint ring 8, is provided. The distal end rigid concave portion 21a is a shape portion projecting further in an outer diameter direction than a peripheral circumferential surface (the peripheral circumferential surface is inserted into an inner circumferential side of the first joint ring 8) and is formed in a concave shape recessed toward a proximal end side in the axial direction. A flange-like portion 21d is connected in a circumferential direction of the distal end rigid concave portion 21a.

A channel receiving member 22 is disposed on an inner side of the distal end rigid member 21. A flange portion 22a projecting outward is formed in a middle of a circumferential surface of the channel receiving member 22. As shown in FIG. 3, a step portion 22c is formed on a proximal end side of the flange portion 22a. The step portion 22c is a shape portion with which a distal end of the channel tube 24 collides when the channel tube 24 is fit in an outer circumferential side of the channel receiving member 22. With such a configuration, when a proximal end side outer circumferential surface 22d of the channel receiving member 22 and a distal end side inner circumferential surface 24a of the channel tube 24 and a contact portion of the step portion 22c and the distal end of the channel tube 24 are bonded, it is possible to effectively prevent an adhesive from adhering to a surface 22b on the proximal end side of the flange portion 22a.

Further, in the distal end rigid concave portion 21a, a pair of inner side end faces 21b in the axial direction and an inner distal end face 21c that connects the two inner side end faces 21b are provided. The pair of inner side end faces 21b is end faces for performing positioning in the circumferential direction of the distal end rigid member 21 and the first joint ring 8 by fitting with a below-mentioned joint ring convex portion 8a of the first joint ring 8.

On the other hand, a cutout formed in a substantial W shape toward a distal end side in the axial direction is provided at a distal end of the first joint ring 8 of the bending tube 9. A convex portion projected toward the distal end side in the axial direction in a center portion of the substantially W shape cutout is the joint ring convex portion 8a that fit in the distal end rigid concave portion 21a to perform positioning. Concave portions adjacent to both sides in the circumferential direction near the joint ring convex portion 8a are joint ring concave portions 8d provided to prevent deformation of the joint ring convex portion 8a due to plastic deformation such as bulge processing as explained below.

A pair of side end faces 8b extending along the axial direction that comes into contact with the pair of inner side end faces 21b of the distal end rigid concave portion 21a to perform positioning in the circumferential direction of the distal end rigid member 21 and the first joint ring 8 is provided in the joint ring convex portion 8a. A distal end face 8c connects the pair of side end faces 8b. Note that it is also possible to bring the distal end face 8c of the joint ring convex portion 8a and the inner distal end face 21c of the distal end rigid concave portion 21a into contact with each other to perform positioning in the axial direction. However, in the present embodiment, the positioning in the axial direction is performed via an axial direction positioning convex portion 22e (see FIG. 2) further extended in an outer diameter direction from the flange portion 22a of the channel receiving member 22.

In the first joint ring 8, a bulge shape portion 8e formed by the bulge processing and wire guide portions 8f (see FIGS. 16 to 19 as well) molded out to an inner diameter side in order to slidably insert through the angle wires 23 are provided.

On a proximal end side of the first joint ring 8, a pair of proximal end coupling portions 8g forming a thin plate-like convex portion for turnably coupling the first joint ring 8 to the second joint ring 8 connected thereto is extended. That is, the proximal end coupling portions 8g having holes of the first joint ring 8 is configured to enable turnable coupling by being superimposed with distal end coupling portions 8h (see FIGS. 16 to 19) having holes extended from a distal end side of the second joint ring 8 to pierce rivets 27 (see FIGS. 16 to 19) through the respective holes in common.

Figure 4:
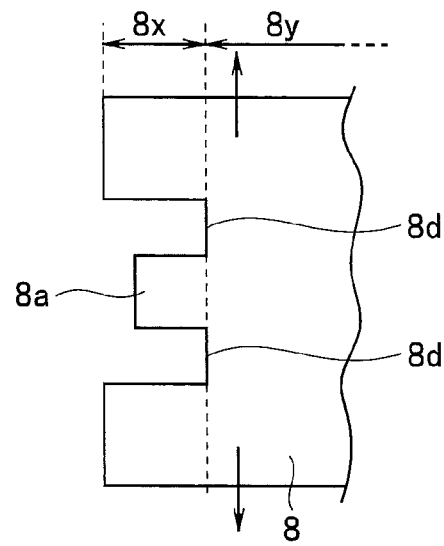
FIG. 4 is a diagram showing a joint ring convex portion and a joint ring concave portion before bulge processing in the first embodiment.
Figure 5:
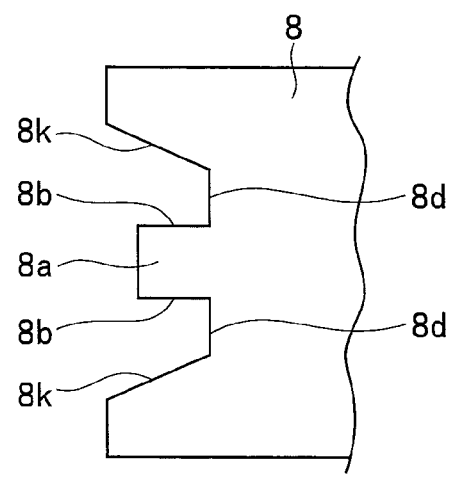
FIG. 5 is a diagram showing the joint ring convex portion and the joint ring concave portion after the bulge processing in the first embodiment.
Figure 6:
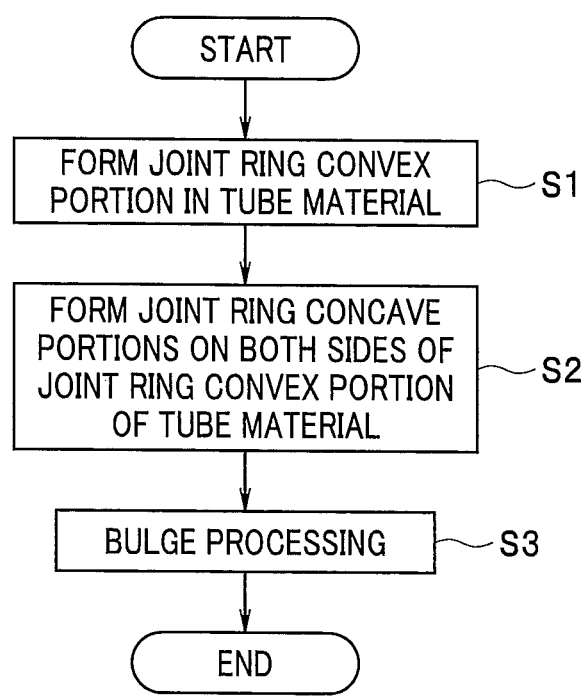
FIG. 6 is a flowchart showing a manufacturing method for a joint ring using the bulge processing in the first embodiment.

Next, a process for using the bulge processing is explained with reference to FIG. 6. A shape change near the joint ring convex portion 8a due to the bulge processing is explained with reference to FIGS. 4 and 5. FIG. 4 is a diagram showing the joint ring convex portion 8a and the joint ring concave portions 8d before the bulge processing. FIG. 5 is a diagram showing the joint ring convex portion 8a and the joint ring concave portions 8d after the bulge processing. FIG. 6 is a flowchart showing a manufacturing method for a joint ring using the bulge processing. Note that the bulge processing is explained as an example of the plastic deformation. However, the plastic deformation may be performed by other machining methods.

As shown in FIG. 6, first, in a tube material, the joint ring convex portion 8a protrudingly provided toward the distal end side in the axial direction that fits in the distal end rigid concave portion 21a provided in the distal end rigid member 21 to perform positioning is formed (step S1).

Further, in the tube material in which the joint ring convex portion 8a is formed, the joint ring concave portions 8d are formed to be adjacent to both sides in the circumferential direction near the joint ring convex portion 8a (step S2).

The joint ring convex portion 8a is formed first and then the joint ring concave portions 8d are formed. However, the joint ring convex portion 8a and the joint ring concave portions 8d may be formed in opposite order or may be simultaneously formed.

Thereafter, the bulge processing is applied to the tube material in which the joint ring convex portion 8a and the joint ring concave portions 8d are formed, whereby the first joint ring 8 shown in FIG. 2 in which the bulge shape portion 8e is formed is manufactured (step S3).

As explained above, the bulge processing means pressing for performing blow molding by causing a material to flow while extending the material to have a shape formed in the mold. Therefore, stress in the outer diameter direction is applied to a tube material proximal end side 8y (a portion where the joint ring convex portion 8a and the joint ring concave portions 8d are not provided as shown in FIG. 4) of the tube material to be subjected to the bulge processing. Plastic deformation stretched along a circumferential surface indicated by an arrow in FIG. 4 occurs on the tube material proximal end side 8y.

On the other hand, since the joint ring concave portions 8d are provided, force of stretching along the circumferential surface is divided by the joint ring concave portion 8d and hardly reaches the joint ring convex portion 8a on a tube material distal end side 8x. As shown in FIG. 5, a shape before the bulge processing is generally maintained. In other portions on the tube material distal end side 8x, an influence of the force of stretching along the circumferential surface of the tube material proximal end side 8y weakens toward the distal end side. Inclined end faces indicated by reference sign 8k in FIG. 5 are formed.

In this way, the joint ring concave portions 8d are provided adjacent to both the circumferential direction sides near the joint ring convex portion 8a before the bulge processing. Consequently, it is possible to prevent deformation of the joint ring convex portion 8a and maintain accuracy in bulge processing the tube material in which the joint ring convex portion 8a is provided.

Next, modifications of the joint ring 8 before the bulge processing is explained with reference to FIGS. 7 to 15. FIGS. 7 to 15 are diagrams showing first to ninth modifications of the joint ring 8 before the bulge processing. Note that, in FIGS. 7 to 15, portions desired to be prevented from being deformed are hatched.

Figure 7:
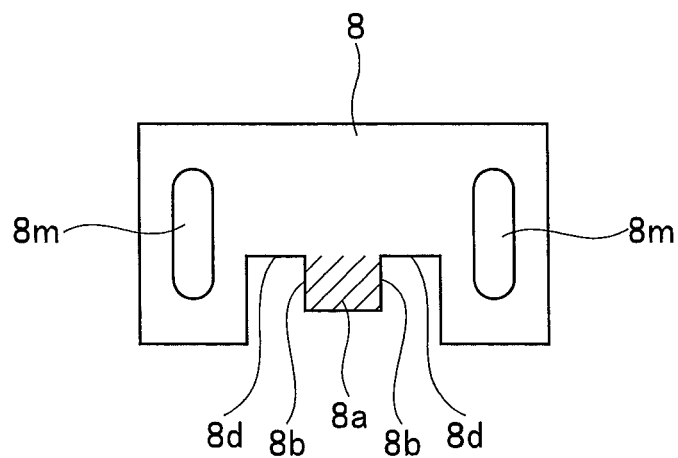
FIG. 7 is a diagram showing a first modification of the joint ring before the bulge processing in the first embodiment.

First, in the first modification shown in FIG. 7, long holes 8m in the axial direction are further formed in the joint ring 8 shown in FIG. 4. The long holes 8m are holes provided in the tube material before plastic deformation in order to prevent deformation of the joint ring convex portion 8a in plastically deforming the tube material.

Figure 8:
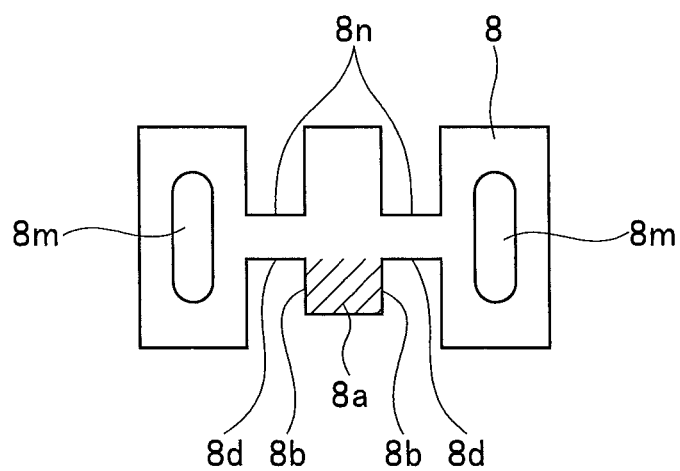
FIG. 8 is a diagram showing a second modification of the joint ring before the bulge processing in the first embodiment.
Figure 9:
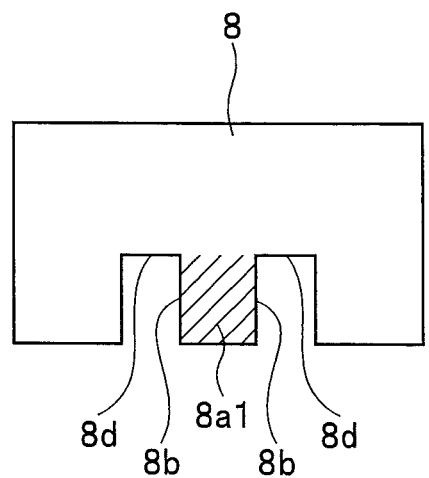
FIG. 9 is a diagram showing a third modification of the joint ring before the bulge processing in the first embodiment.
Figure 10:
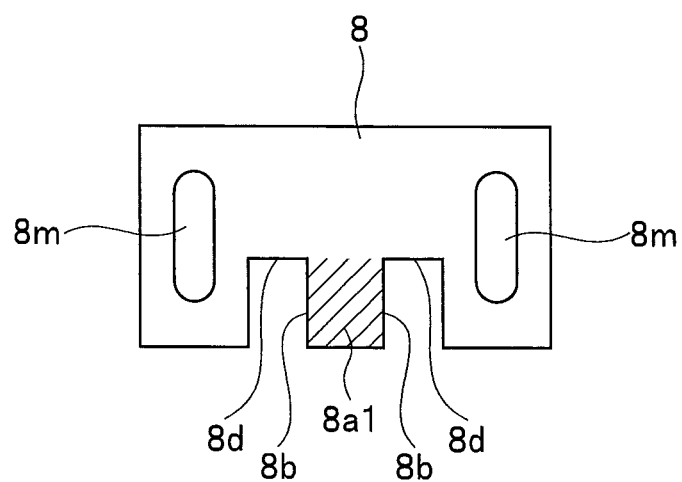
FIG. 10 is a diagram showing a fourth modification of the joint ring before the bulge processing in the first embodiment.
Figure 11:
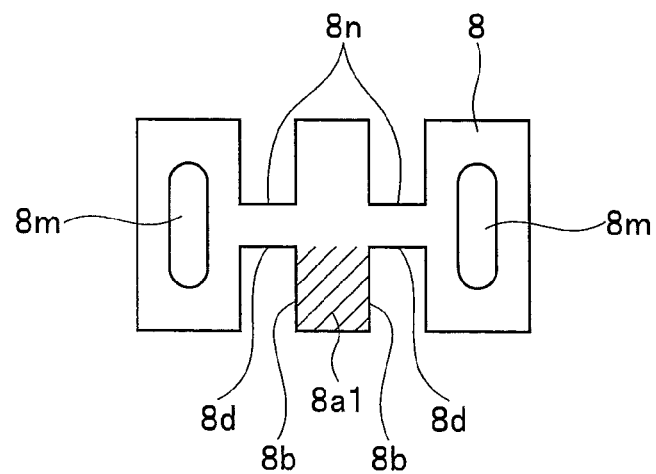
FIG. 11 is a diagram showing a fifth modification of the joint ring before the bulge processing in the first embodiment.

In the second modification shown in FIG. 8, proximal end side joint ring concave portions 8n are further formed in the joint ring 8 shown in FIG. 7. The proximal end side joint ring concave portions 8n are opposite end concave portions for preventing deformation of the joint ring convex portion 8a in plastically deforming the tube material. The opposite end concave portions are cut out before the plastic deformation from a proximal end to a distal end side of the tube material (more generally, at an end on an opposite side in the axial direction of the joint ring convex portion 8a of the tube material).

In the examples shown in FIGS. 4, 7, and 8, the joint ring convex portion 8a is located further on the proximal end side than a distal end face of the first joint ring 8 itself. On the other hand, in the third to fifth modifications shown in FIGS. 9 to 11, a distal end face of a joint ring convex portion 8a1 is substantially flush with the distal end face of the first joint ring 8 itself. In the third modification shown in FIG. 9, the joint ring concave portions 8d are formed. In the fourth modification shown in FIG. 10, the long holes 8m in the axial direction are further formed. In the fifth modification shown in FIG. 11, the proximal end side joint ring concave portions 8n are further formed.

Figure 12:
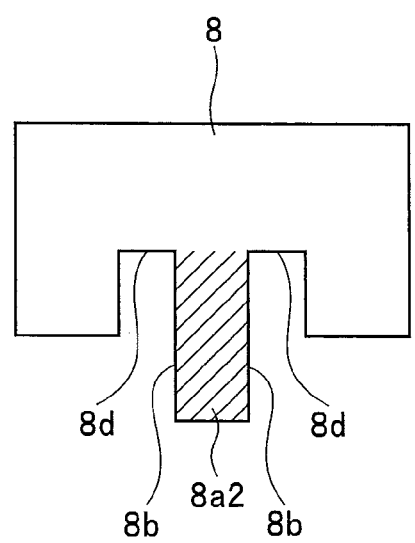
FIG. 12 is a diagram showing a sixth modification of the joint ring before the bulge processing in the first embodiment.
Figure 13:
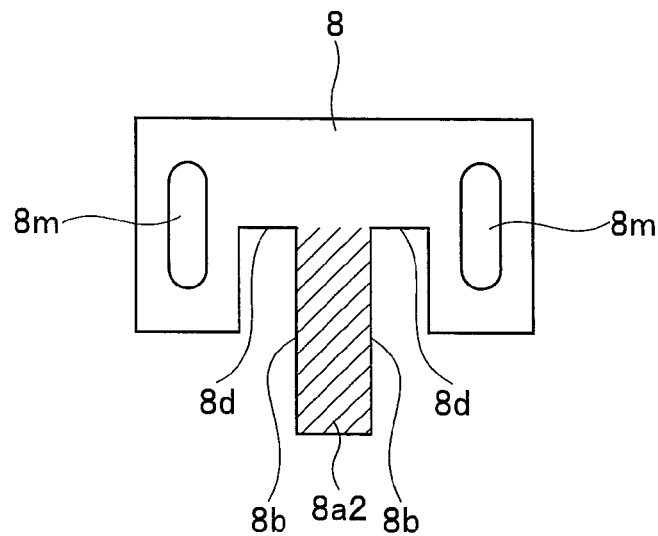
FIG. 13 is a diagram showing a seventh modification of the joint ring before the bulge processing in the first embodiment.
Figure 14:
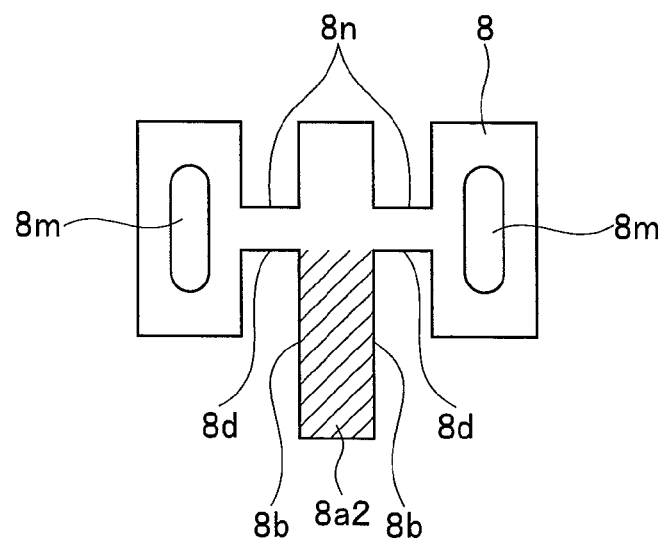
FIG. 14 is a diagram showing an eighth modification of the joint ring before the bulge processing in the first embodiment.

On the other hand, in the sixth to eighth modifications shown in FIGS. 12 to 14, a distal end face of a joint ring convex portion 8a2 projects further to the distal end side than the distal end face of the first joint ring 8 itself. In the sixth modification shown in FIG. 12, the joint ring concave portions 8d are formed. In the seventh modification shown in FIG. 13, the long holes 8m in the axial direction are further formed. In the eighth modification shown in FIG. 14, the proximal end side joint ring concave portions 8n are further formed.

Figure 15:
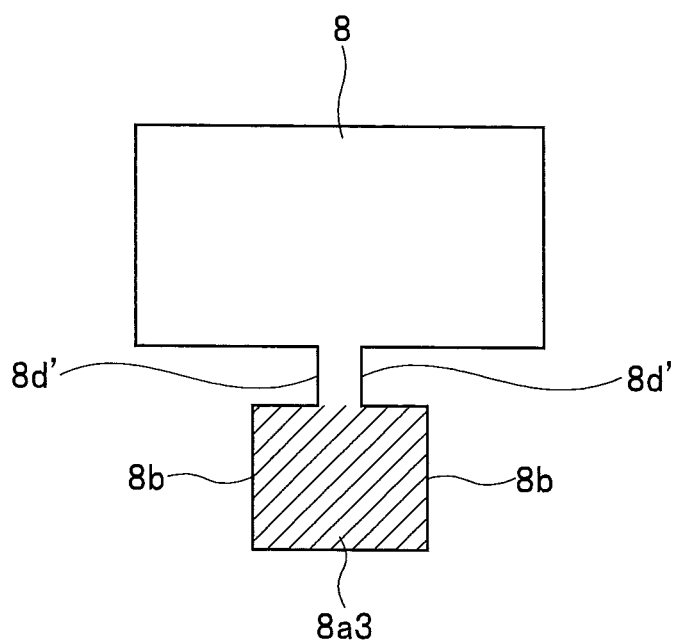
FIG. 15 is a diagram showing a ninth modification of the joint ring before the bulge processing in the first embodiment.

In the ninth modification shown in FIG. 15, an arrangement of joint ring concave portions 8d' is different from the joint ring concave portions 8d. The joint ring concave portions 8d' are concave portions in circumferential direction provided near a proximal end side of a joint ring convex portion 8a3 to sandwich a connecting portion of the joint ring convex portion 8a3 and a tube material portion further on the proximal end side than the joint ring convex portion 8a3. Note that it goes without saying that, in a configuration shown in FIG. 15, the long holes 8m in the axial direction and the proximal end side joint ring concave portions 8n may be formed.

Note that, in the above explanation, a fitting shape of the first joint ring 8 and the distal end rigid member 21 is mainly explained. However, if the distal end side and the proximal end side in the respective figures are replaced, the explanation can be applied in the same manner to a fitting shape of the joint ring 8 on a most distal end side (referred to as last joint ring 8 or the like as appropriate) among the plurality of joint rings 8 configuring the bending tube 9 and a rigid member provided at a distal end of the flexible portion 7. Further, when one or more rigid members are provided halfway in the bending tube 9, that is, when the bending tube 9 is divided into a plurality of bending tube portions such as a first bending tube portion and a second bending tube portion by the one or more rigid members, the above-mentioned fitting shape can be applied to fitting of the respective bending tube portions and the rigid member. Therefore, the rigid member is not limited to the distal end rigid member 21 and the rigid concave portion is not limited to the distal end rigid concave portion 21a. Fitting of the rigid member and a joint ring provided in a position adjacent to the rigid member is not only performed on the distal end side in the axial direction but also performed on the proximal end side in the axial direction.

Figure 16:
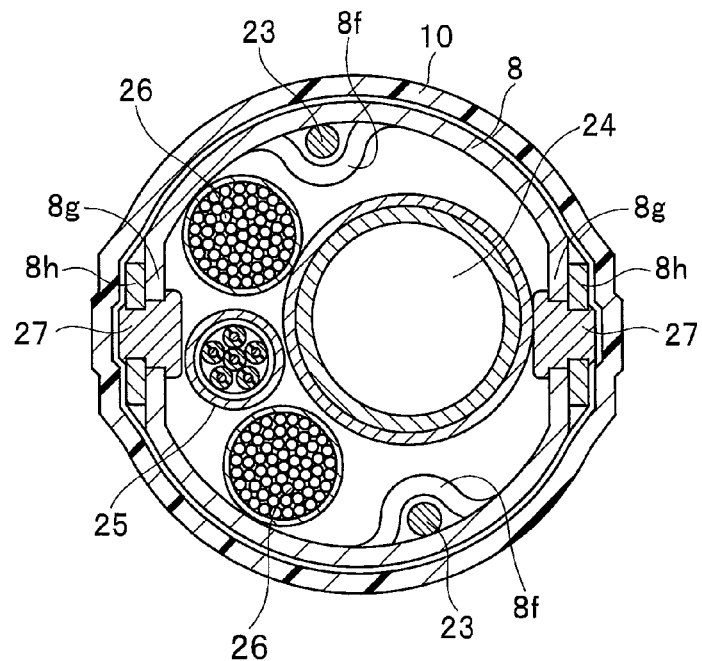
FIG. 16 is a diagram showing an example of an internal structure of a bending tube at the time when joint rings are coupled to each other using a pair of general rivets in the first embodiment.
Figure 17:
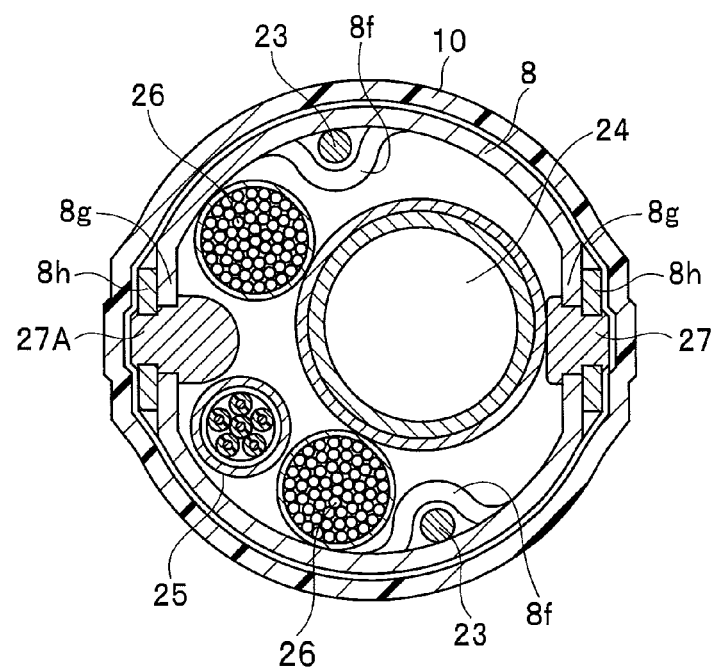
FIG. 17 is a diagram showing an example of an internal structure of the bending tube at the time when one rivet is a spherical head rivet in the first embodiment.
Figure 18:
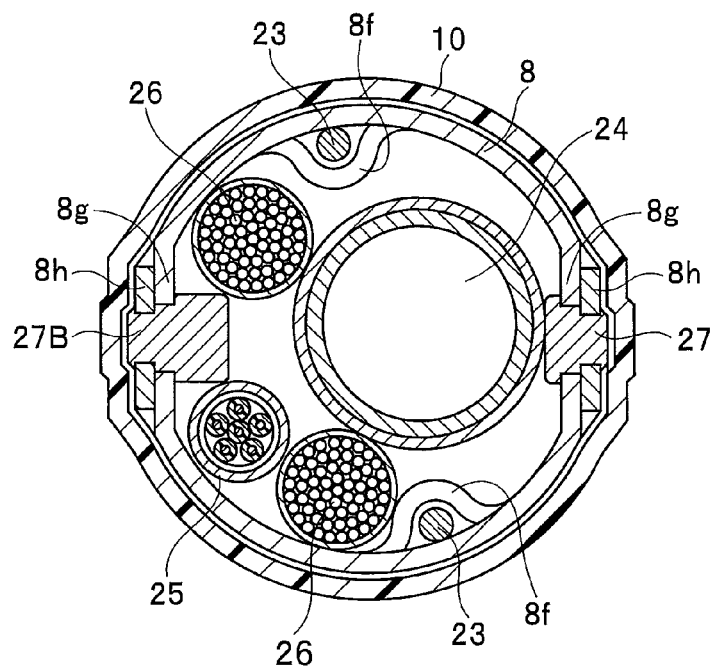
FIG. 18 is a diagram showing an example of an internal structure of the bending tube at the time when one rivet is a columnar head rivet in the first embodiment.
Figure 19:
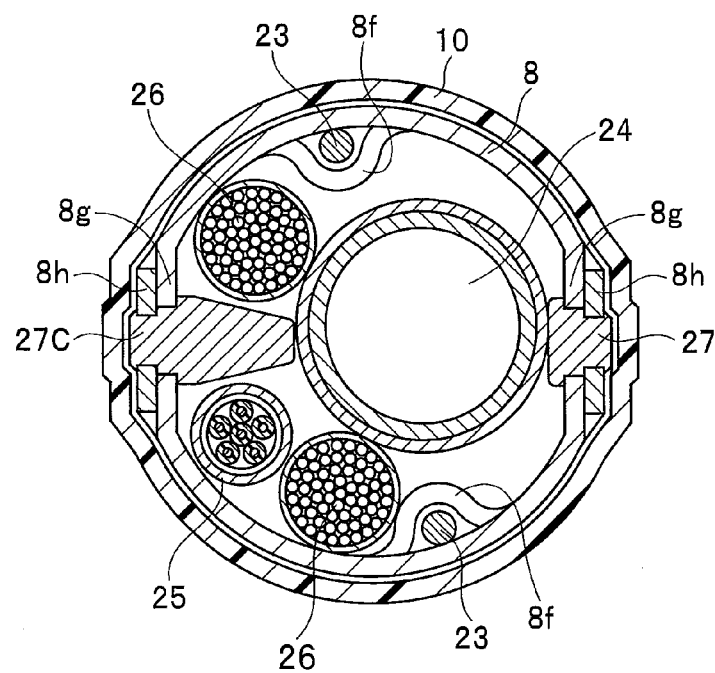
FIG. 19 is a diagram showing an example of an internal structure of the bending tube at the time when one rivet is a truncated conic head rivet in the first embodiment.

Subsequently, an internal structure of the bending tube 9 is explained with reference to FIGS. 16 to 19. FIG. 16 is a diagram showing an example of an internal structure of the bending tube 9 at the time when the joint rings 8 are coupled to each other using a pair of general rivets 27. FIG. 17 is a diagram showing an example of an internal structure of the bending tube 9 at the time when one rivet is a spherical head rivet 27A. FIG. 18 is a diagram showing an example of an internal structure of the bending tube 9 at the time when one rivet is a columnar head rivet 27B. FIG. 19 is a diagram showing an example of an internal structure of the bending tube 9 at the time when one rivet is a truncated conic head rivet 27C.

A small-diameter electronic endoscope including a bending mechanism in two directions (e.g., up/down directions) generally includes two angle wires 23, a channel tube 24, an image pickup cable 25, and two light guide fibers 26 as built-in articles of the insertion portion 3. Further, on an inner diameter side of the joint ring 8, the wire guide portions 8f and the rivets 27 for turnably coupling the proximal end coupling portions 8g and the distal end coupling portions 8h are protrudingly provided (heads of the rivets 27 are located on an inner diameter side in order to prevent projection to an external shape side).

In such a configuration, in the case of the internal structure of the bending tube 9 in which the joint rings 8 are coupled to each other using the general rivets 27 shown in FIG. 16, if bending operation is performed, it is likely that the built-in articles interfere with one another or, in some case, a positional relation (a layout) of the built-in articles changes or the built-in articles are entwined (or narrowed). Further, there is also concern that a bend or buckling occurs in the light guide fibers 26 or the image pickup cable 25 is tensed and a load is applied to a portion where the image pickup cable 25 is fixed.

Configuration examples for solving such problems are configuration examples shown in FIGS. 17 to 19. FIG. 17 is an example in which the spherical head rivet 27A is used. FIG. 18 is an example in which a columnar head rivet 27B is used. FIG. 19 is an example in which the truncated conic head rivet 27C is used. The rivets 27A to 27C have longer heads than the general rivet 27.

First, in the bending portion 6, the channel tube 24, the first light guide fiber 26, the image pickup cable 25, and the second light guide fiber 26 are arranged counterclockwise in this order.

In such an arrangement, as a rivet located near the channel tube 24 having a largest diameter of a pair of rivets, the general rivet 27 is used. On the other hand, as the other rivet, in an arrangement example in the present embodiment, as a rivet located near the image pickup cable 25, any one of the rivets 27A to 27C shown in FIGS. 17 to 19 (hereinafter referred to as streamlined rivets) is used.

In this case, the two light guide fibers 26 are separated by the channel tube 24 having the largest diameter. One light guide fiber 26 and the image pickup cable 25 are separated from the other light guide fiber 26 by any one of the streamlined rivets 27A to 27C.

With such an arrangement and a configuration, the small-diameter built-in articles in which entanglement and the like relatively easily occur, i.e., the two light guide fibers 26 and the image pickup cable 25 are separated into two groups and substantially prohibited from moving to deviate from specific regions. Therefore, it is possible to effectively prevent the entanglement and the like.

Note that the several examples of the streamlined rivets for preventing entanglement and the like are shown in FIGS. 17 to 19. However, the streamlined rivets are not limited to these. A head shape of the streamlined rivets only has to be a protrusion larger in a head length than the general rivet 27 and formed in a streamlined shape.

A total number of rivets used in the bending tube 9 is (the number of joint rings−1) pairs. However, at least one of the rivets only has to be the streamlined rivet.

Figure 20:
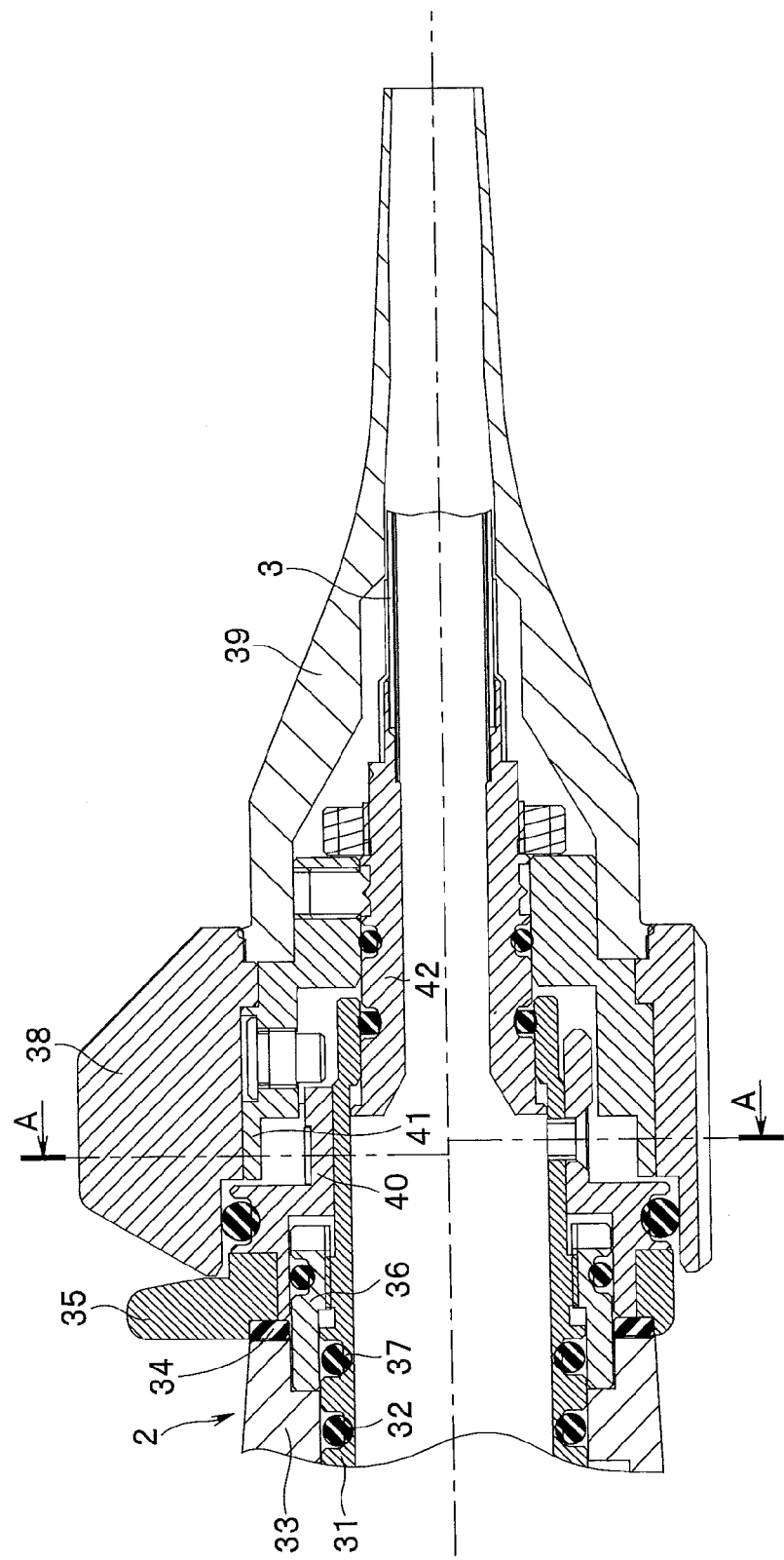
FIG. 20 is a sectional view taken along the axial direction of a main part of an operation portion in the first embodiment.
Figure 21:
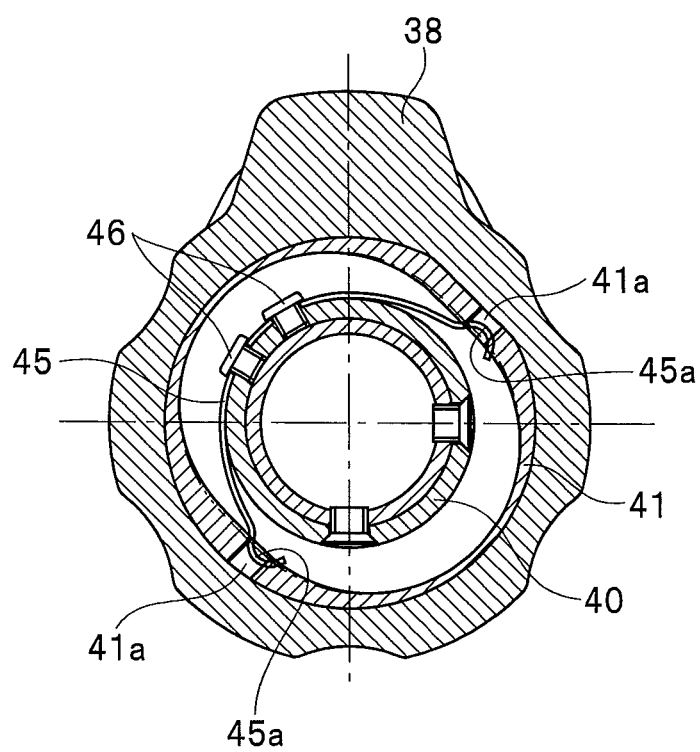
FIG. 21 is an A-A sectional view in FIG. 20 in the first embodiment.

Next, several points of an internal structure of the operation portion 2 are explained with reference to FIGS. 20 and 21. FIG. 20 is a sectional view taken along the axial direction of a main part of the operation portion 2. FIG. 21 is an A-A sectional view in FIG. 20.

As shown in FIG. 20, an operation portion side cap 31 is provided on an inside of the operation portion 2. An operation portion armor 33 is disposed in an outer circumference of the operation portion side cap 31 via an O ring 32. An UP bending indicator 35 related to bending operation is provided on a distal end side of the operation portion armor 33. A rubber member 34 is disposed between the distal end of the operation portion armor 33 and the UP bending indicator 35 as an elastic member for performing sealing. On an inner circumference side of the rubber member 34, a rubber stop member 36 is arranged to prevent the rubber member 34 from sticking out to the inner circumferential side even if the rubber member 34 is compressed. The rubber stop member 36 is disposed on an outer circumference side of the operation portion side cap 31 via an O ring 37.

On a distal end side of the UP bending indicator 35, an insertion portion rotating dial 38 for rotating the insertion portion 3 about an axis is disposed. A further distal end side of the insertion portion rotating dial 38 is a bending preventing portion 39 for preventing a bend of the insertion portion 3.

On an outer circumference side of a frame member 40 provided in a distal end side outer circumference of the operation portion side cap 31, as shown in FIG. 21, an elastic member 45 formed by a leaf spring or the like having length equivalent to a half circumference along a circumferential direction is attached via screws 46 or the like. The elastic member 45 is disposed between the frame member 40 and a frame member 41 provided on an inner circumference side of the insertion portion rotating dial 38. Engaging convex portions 45a formed to be convex in an outer circumferential direction are respectively formed at both end portions in the circumferential direction of the elastic member 45. On the other hand, engaging concave portions 41a are formed on an inner circumference side of the frame member 41. When the insertion portion rotating dial 38 is rotated about the axis, the engaging concave portions 41a also integrally rotate and engage with the engaging convex portions 45a of the elastic member 45 in predetermined rotating positions. With such a configuration, the insertion portion rotating dial 38 is configured to generate a sense of grip in the predetermined rotating positions in the circumferential direction.

Further, a distal end portion of the operation portion side cap 31 engages with a proximal end portion of the insertion portion cap 42. The insertion portion cap 42 is provided on a proximal end side of the insertion portion 3.

According to such a first embodiment, since the joint ring concave portions 8d are provided before the bulge processing near the joint ring convex portion 8a for positioning with the distal end rigid member 21 (e.g., adjacent to both sides in the circumferential direction), it is possible to prevent deformation of the joint ring convex portion 8a even after the bulge processing and maintain accuracy. Therefore, it is possible to perform the fitting of the first joint ring 8 and the distal end rigid member 21 without deviation and with high positioning accuracy.

Further, since the joint ring convex portion 8a and the joint ring concave portions 8d are formed before the bulge processing, a mold for holding a tube material in forming the shape portions can be changed to an inexpensive one or can be made unnecessary. Therefore, it is unnecessary to use a mold having a complicated shape. It is possible to inexpensively perform manufacturing of the joint ring 8.

Second Embodiment

Figure 22:
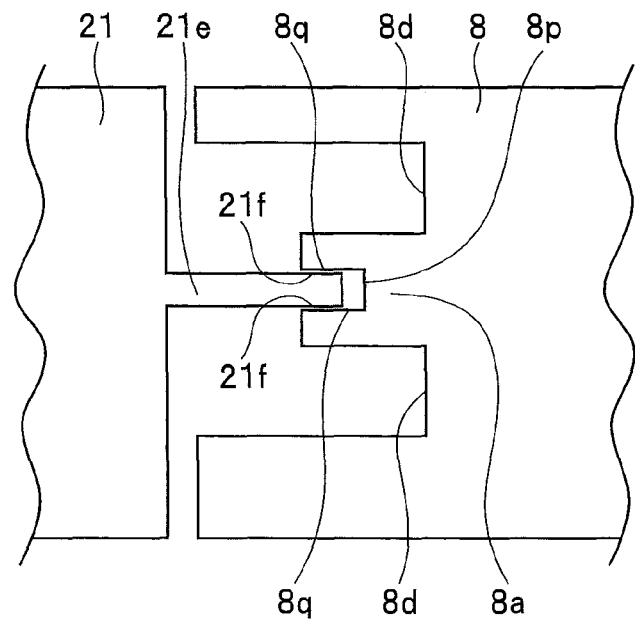
FIG. 22 is a side view showing a connection structure of a distal end rigid member and a first joint ring in a second embodiment of the present invention.

FIG. 22 is a diagram showing a second embodiment of the present invention and is a side view showing a connection structure of a distal end rigid member and a first joint ring. In the second embodiment, components same as the components in the first embodiment are denoted by the same reference numerals and signs and explanation of the components is omitted. Differences from the first embodiment are mainly explained.

Figure 23:
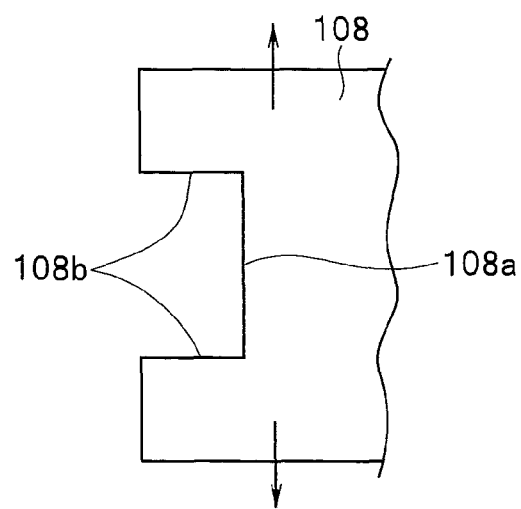
FIG. 23 is a side view showing a joint ring before bulge processing in the related art.
Figure 24:
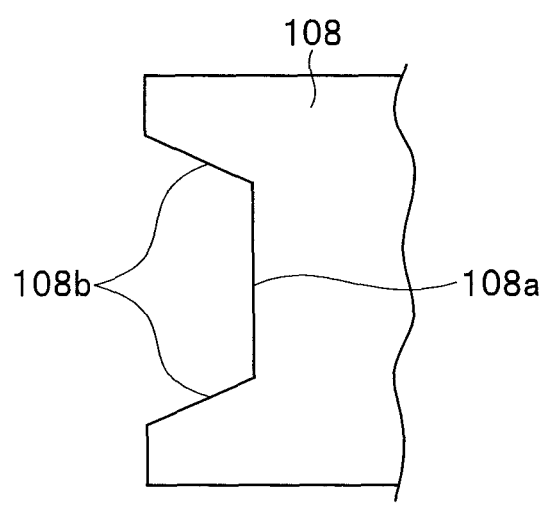
FIG. 24 is a side view showing the joint ring after the bulge processing in the related art.

In the first embodiment, the shape portions for positioning for performing positioning in the circumferential direction are the concave portion on the rigid member side and the convex portions on the joint ring side. On the other hand, in the second embodiment, the rigid member side is the convex portion and the joint ring side is the concave portions. However, if the joint ring side is simply formed as the concave portions, as it is seen when FIGS. 23 and 24 are referred to, it is likely that the side end faces 8b for positioning are deformed by plastic deformation. Therefore, in the present embodiment, a concave portion for positioning is provided in a convex portion functioning as a shape portion prevented from being plastically deformed.

That is, as explained above, the joint ring concave portions 8d are provided on both sides in the circumferential direction of the joint ring convex portion 8a of the first joint ring 8. Further, a concave portion 8p is provided at an axial direction distal end portion of the joint ring convex portion 8a. Inner side end faces 8q of the concave portion 8p are end faces for positioning for playing a function same as the function of the side end faces 8b.

On the other hand, a rigid convex portion 21e for positioning is projected toward an axial direction proximal end side from the distal end rigid member 21. Both side end faces 21f of the rigid convex portion 21e fit with the inner side end faces 8q of the concave portion 8p to perform positioning in the circumferential direction.

Note that, as in the first embodiment, for example, the joint ring 8 for positioning is not limited to the first joint ring 8 and the distal end side and the proximal end side may be replaced.

According to such a second embodiment, effects substantially the same as the effects in the first embodiment can be attained by forming the rigid member side as the convex portion and forming the joint ring side as the concave portion provided in the convex portion in which plastic deformation is prevented.

Note that the present invention is not limited to the embodiments per se. In an implementation stage, it is possible to modify and embody the elements without departing from the spirit of the present invention. It is possible to form various modes of the invention according to appropriate combinations of the plural elements disclosed in the embodiments. For example, several elements may be deleted from all the elements disclosed in the embodiments. Further, the embodiments disclosed in the different embodiments may be combined. In this way, it goes without saying that various modifications and applications are possible within a range not departing from the gist of the invention.

What is claimed is:

1. A joint ring for an endoscope bending tube configured to fit with and to be fixed to a rigid member on a distal end side or a proximal end side in an axial direction, the joint ring comprising:

a joint ring convex portion provided in a tube material and protrudingly provided toward the distal end side or the proximal end side in the axial direction, the joint ring convex portion including side end faces that fit with a positioning shape portion provided in the rigid member to perform positioning in a circumferential direction;

a plastically deformed shape portion provided in the joint ring at an axial direction position outside of an axial direction position of the joint ring convex portion and at a circumferential direction position outside of a circumferential direction position of the joint ring convex portion, such that the axial direction position of the plastically deformed shape portion overlaps the axial direction position of the joint ring convex portion and is formed by being plastically deformed by at least a stretching force of stretching along a circumferential surface of the tube material; and joint ring concave portions constituted by concave shape portions arranged near both sides in the circumferential direction of the joint ring convex portion between the plastically deformed shape portion and the joint ring convex portion in the tube material, and configured, when the plastically deformed shape portion is plastically deformed by the stretching force of stretching along the circumferential surface of the tube material, to interrupt transmission of deforming force of the tube material with the plastic deformation in the plastically deformed shape portion by the concave shape portion to keep the deforming force from reaching the joint ring convex portion to thereby prevent deformation of the joint ring convex portion caused by the plastic deformation in the plastically deformed shape portion.

2. The joint ring according to claim 1, wherein
the positioning shape portion provided in the rigid member is a rigid concave portion, and
the side end faces included in the joint ring convex portion are side end faces in the circumferential direction of the joint ring convex portion.

3. The joint ring according to claim 2, wherein the joint ring concave portions are concave portions in the axial direction provided to be adjacent to both sides in the circumferential direction of the joint ring convex portion.

4. The joint ring according to claim 2, further comprising holes provided in the tube material before the plastic deformation in order to prevent deformation of the joint ring convex portion in plastically deforming the tube material in which the joint ring convex portion is provided.

5. The joint ring according to claim 2, further comprising opposite end concave portions for preventing deformation of the joint ring convex portion in plastically deforming the tube material in which the joint ring convex portion is provided, the opposite end concave portions being cut out before the plastic deformation at an end on an axial direction opposite side of the joint ring convex portion in the tube material.

6. The joint ring according to claim 2, wherein the joint ring concave portions are concave portions in the circumferential direction provided on a proximal end side or a distal end side of the joint ring convex portion to sandwich a connecting portion of the joint ring convex portion and a tube material portion which is proximal or distal with respect to the joint ring convex portion.

7. The joint ring according to claim 1, wherein
the positioning shape portion provided in the rigid member is a rigid convex portion, and
the joint ring convex portion further includes a concave portion at a distal end portion thereof, the side end faces included in the joint ring convex portion being inner side end faces in the circumferential direction of the concave portion.

8. A bending tube of an endoscope configured by turnably coupling a plurality of joint rings, wherein
a joint ring provided in a position adjacent to the rigid member according to claim 1 is the joint ring for positioning according to claim 1.

9. An endoscope comprising:
the bending tube according to claim 8; and
the rigid member including the positioning shape portion that fits with the side end faces included in the joint ring convex portion of the joint ring for positioning to perform positioning.

10. A manufacturing method for a joint ring for an endoscope bending tube comprising:
forming, in a tube material, a joint ring convex portion protrudingly provided toward a distal end side or a proximal end side in an axial direction, the joint ring convex portion including side end faces that fit with a positioning shape portion provided in a rigid member to perform positioning in a circumferential direction, and joint ring concave portions located near the joint ring convex portion; and
plastically deforming the tube material in which the joint ring convex portion and the joint ring concave portions are formed and forming a plastically deformed shape portion at an axial direction position outside of an axial direction position of the joint ring convex portion and at a circumferential direction position outside of a circumferential direction position of the joint ring convex portion with a force of stretching along a circumferential surface of the tube material in the plastic deformation such that the axial direction position of the plastically deformed shape portion overlaps the axial direction position of the joint ring convex portion,
the joint ring concave portions being provided near both sides in the circumferential direction of the joint ring convex portion between the plastically deformed shape portion of the tube material and the joint ring convex portion to block all lines in the circumferential direction connecting the plastically deformed shape portion and the joint ring convex portion and interrupting the force of stretching along the circumferential surface to keep the force from reaching the joint ring convex portion to thereby prevent deformation of the joint ring convex portion due to the plastic deformation.

11. A manufacturing method for a joint ring for an endoscope bending tube, comprising:
forming, in a tube material, a joint ring convex portion protrudingly provided toward a distal end side or a proximal end side in an axial direction, the joint ring convex portion including side end faces that fit with a positioning shape portion provided in a rigid member to perform positioning in a circumferential direction, and joint ring concave portions located near the joint ring convex portion; and
plastically deforming the tube material in which the joint ring convex portion and the joint ring concave portions are formed and forming a plastically deformed shape portion at an axial direction position outside of an axial direction position of the joint ring convex portion and at a circumferential direction position outside of a circumferential direction position of the joint ring convex portion such that the axial direction position of the plastically deformed shape portion overlaps the axial direction position of the joint ring convex portion,
wherein the joint ring concave portions prevent deformation of the joint ring convex portion in the plastic deformation.

* * * * *